United States Patent
Hanson et al.

(10) Patent No.: US 7,227,042 B2
(45) Date of Patent: Jun. 5, 2007

(54) METHOD OF PREPARING 1-ACETYL-1-CHLOROCYCLOPROPANE

(75) Inventors: Joe J. Hanson, Holt, MO (US); David M. Mayes, Overland Park, KS (US); Klaus Stroech, Solingen (DE); Shekhar V. Kulkarni, Overland Park, KS (US)

(73) Assignees: Bayer CropScience LP, Research Triangle Park, NC (US); Bayer CropScience Aktiengesellschaft, Monheim (DE)

( * ) Notice: Subject to any disclaimer, the term of this patent is extended or adjusted under 35 U.S.C. 154(b) by 428 days.

(21) Appl. No.: 10/818,689

(22) Filed: Apr. 6, 2004

(65) Prior Publication Data

US 2005/0222451 A1 Oct. 6, 2005

(51) Int. Cl.
*C07C 49/00* (2006.01)
*C07C 45/00* (2006.01)

(52) U.S. Cl. ...................... 568/316; 568/303

(58) Field of Classification Search ............... 560/231; 568/316, 303
See application file for complete search history.

(56) References Cited

OTHER PUBLICATIONS

Michael et al , Advanced Organic chemistry, 5th ed., 2001, p. 454-456.*
Database CA 'Online! Chemical Abstracts Service, Columbus, Ohio, US; Vinogradov, M.G. et al: "Oxidative addition of 1,3-dicarbonyl compounds to olefins in the presence of the manganese(III) acetate/lithium chloride system and synthesis of functionally substituted cyclopropanes" XP002334791 retrieved from STN Database accession No. 1984:209194 abstract & Izvestiya Akademii Nauk SSSR, Seriya Khimicheskaya, (2), 375-83 Coden: IASKA6; ISSN: 0002-3353, 1984 & Vinogradov, M.G.; Dolinko, V.I.; Nikishin, G.I.: Bull. Acad. Sci. USSR Div. Chem. Sci. (Engl. Transl.); 33, 1984, pp. 334-341.
Fitjer, Lutz: "1,1-Bifunctional cyclopropanes; convenient synthesis of 1-bromo- 1-chloro- and 1-fluorocyclopropyl methyl ketone" Synthesis, (3), 189-91 CODEN SYNTBF; ISSN: 0039-7881, 1977, XP002334549.

* cited by examiner

*Primary Examiner*—Taylor Victor Oh
(74) *Attorney, Agent, or Firm*—Richard E. L. Henderson

(57) ABSTRACT

The present invention provides a method of preparing 1-acetyl-1-chlorocyclopropane from 1,3 dichloro-2-pentanone by reaction with base in the presence of a phase transfer catalyst. The reaction may be run in the presence or absence of an organic solvent and in a continuous or batch process.

26 Claims, No Drawings

METHOD OF PREPARING 1-ACETYL-1-CHLOROCYCLOPROPANE

BACKGROUND OF THE INVENTION

The present invention relates to the preparation of 1-acetyl-1-chlorocyclopropane from 3,5-dichloro-2-pentanone.

It is known that treatment of 3,5-dichloro-2-pentanone with a base with heating will provide 1-acetyl-1-chlorocyclopropane. However, it is generally acknowledged that such a procedure does not provide acceptable yields.

SUMMARY OF THE INVENTION

The present invention provides a method of preparing 1-acetyl-1-chlorocyclopropane which comprises:
(a) providing 3,5-dichloro-2-pentanone;
(b) providing a phase transfer catalyst;
(c) providing an aqueous solution of a base selected from the group consisting of bases whose conjugate acids have a $pK_a$ value in water of from about 8 to about 15;
(d) admixing 3,5-dichloro-2-pentanone, the phase transfer catalyst and the solution at a temperature above room temperature in the absence of an organic solvent; and
(e) separating the 1-acetyl-1-chlorocyclopropane.

DETAILED DESCRIPTION OF THE INVENTION

The method of the present invention may be carried out in a batch manner or continuously.

The bases used in the method of the present invention include. sodium hydroxide, potassium hydroxide, sodium carbonate, potassium carbonate, sodium phosphate and potassium phosphate. Sodium metal bases are generally preferred. Hydroxide anion bases are preferred. Sodium hydroxide is most preferred. In order to achieve complete conversion of 3,5-dichloro-2-pentanone, the preparation is generally effected with at least a molar equivalent of base relative to the amount of 3,5-dichloro-2-pentanone. Preferably from about 1.1 to about 1.5 molar equivalents of base, more preferably from about 1.1 to about 1.2 molar equivalents of base, are used per mole of 3,5-dichloro-2-pentanone. The concentration of base is generally from about 5% to about 50% by weight of sodium hydroxide, preferably from about 10% to about 30% by weight, more preferably from about 20% to about 25%. A continuous process will generally use the latter range or base concentrations when the base is sodium hydroxide.

The method of the present invention may be carried out in the presence or absence of an organic solvent. When the method of the invention is carried out using hydroxides as base in the absence of an organic solvent, the product must be removed from the reaction mixture within a relatively short time or the excess base in the reaction mixture must be neutralized to minimize the decomposition of the product if there is excess base. However when weaker bases such as carbonates or phosphates are used even in the absence of an organic solvent, the product can remain in the reaction mixture for extended periods of time. In the presence of an excess of hydroxide base and without organic solvent, the product is generally removed immediately after completion of the reaction is detected, e.g., by liquid chromatography (LC) or gas chromatography (GC) analysis.

The reaction takes generally from about 0.1 to about 600 minutes after the completion of admixing. Generally in the absence of solvent, when from about 1 to about 3 mole percent of catalyst and from about 1 to about 1.5 molar equivalents of hydroxide base (20–25% concentration) are used, the reaction is complete in a time from about 0.1 to about 5 minutes after completion of admixing. When a solvent is added, the reaction is completed from about 0.2 to about 5 minutes after completion of admixing. When a hydroxide base is substituted by a carbonate or phosphate anion base, the reaction takes from about 15 to about 120 minutes. When organic solvent is used, the latter reaction time may be extended to a time from about 30 to about 300 minutes.

In the absence of solvent, and when hydroxide bases are used, the reaction is generally stopped from about 1 minute to about 15 minutes after completion of the reaction is determined. When carbonates or phosphates are used, notwithstanding the use of organic solvent, the reaction may be stopped from about 1 to about 120 minutes after the determination of the completion of the reaction.

The present invention also provides a method of preparing 1-acetyl-1-chlorocyclopropane which comprises
(a) providing 3,5-dichloro-2-pentanone;
(b) providing a phase transfer catalyst;
(c) providing an aqueous solution of a base selected from the group consisting of bases whose conjugate acids have a $pK_a$ value in water of from about 8 to about 15;
(d) admixing 3,5-dichloro-2-pentanone, the phase transfer catalyst and the aqueous solution of a base at a temperature above room temperature in the presence of an organic solvent which organic solvent is substantially immiscible in water and which solvent is substantially impervious to the reaction conditions of the method; and
(e) separating the 1-acetyl-1-chlorocyclopropane.

The presence of an organic solvent considerably slows down the decomposition of the product by the excess base. This therefore allows the reaction to be carried out for extended length of time. Thus when the reaction is carried out in the presence of an organic solvent, at the end of the admixing, the reaction is heated until the reaction is complete as determined, e.g., by GC or LC. The excess base is then neutralized with acid and the product separated from the reaction mixture by fractional distillation.

Suitable solvents include monohalobenzenes, dihalobenzenes, e.g., 1,2-dichlorobenzene, dialkyl ethers wherein the alkyl groups of the ether may the same or different and which alkyl groups are from C1 to C12, preferably from C1 to C8; and alkylaryl ethers. Solvents which are suitable for the method of the present invention include those solvents having a miscibility in water of from about 0 grams solvent per 100 mL water at 25° C. (room temperature) to about 3 g/100 mL water; preferably from about 0.01 g/100 mL water to about 1 g/100 mL water. The reaction may be preferably run in the presence of an organic solvent in which 3,5-dichloro-2-pentanone is soluble.

A phase transfer catalyst is necessary for this process since the reactions carried out in the absence of phase transfer catalyst give poor yields even under otherwise optimal reaction conditions. The phase transfer catalyst may be any catalyst suited for that purpose known to one of skill in the art. Water-miscible and water-immiscible catalysts may be employed. Generally tetraalkylammonium halides and aryltrialkylammonium halides are used. Preferably the phase transfer catalyst is selected from the group consisting of tetrabutylammonium halides and methyltrialkylammonium halides. Most preferably the phase transfer catalyst is methyltrioctylammonium chloride and/or methyltributylammonium chloride.

The amount of the catalyst may vary widely. Generally from about 0.1 to about 10 mole percent is used. Preferably from about 1 to about 5 mole % is used. By the term mole % is meant the stoichiometric amount of the catalyst as a percent of the 3,5-dichloro-2-pentanone in moles. For example, if 1 mol of 3,5-dichloro-2-pentanone were reacted, then about 0.03 moles (3 mole %) of catalyst might be used. The weight:weight ratio of 3,5-dichloropentanone to phase transfer catalyst is generally from about 10:1 to about 100:1, preferably about 10:1 to about 30:1 and more preferably about 12:1 to about 16:1.

The solvent is generally chosen so that the boiling point of the solvent at atmospheric pressure is different than that of the boiling temperature of 1-acetyl-1-chlorocyclopropane at atmospheric pressure so that the product can be separated from the solvent by fractional distillation. A preferred solvent is 1,2-dichlorobenzene.

The temperature of the reaction has a significant effect on the performance of the reaction. When hydroxides are used as base, the yield is higher when the reactants are brought into contact with each other at higher temperatures. At lower temperatures, side reactions increase causing the yield of the desired product to decrease substantially. When weaker bases such as carbonates and phosphates are used, the reaction is very slow at lower temperatures and therefore the reaction is preferably carried out under reflux conditions to achieve reasonable rate of reaction. In the case where the reaction is run above room temperature, the reactants may optionally be heated to a temperature of from about 50° C. to about 100° C. at atmospheric pressure. If such pre-heating is done, the optimal temperature is from about 80° C. to about 100° C.

The preparation may also be run continuously. Persons of ordinary skill in the art will understand that the preparation may be run in any suitable vessel that will allow the continuous removal of the product and separation of any by-products. Generally, the mixture is made by admixing the reactants in the absence of an organic solvent in a flow reactor. There is allowed thereafter a short mixing time, generally from about 0.1 minutes to about 60 minutes, preferably from about 0.2 minutes to about 10 minutes, most preferably from about 0.5 minutes to about 2 minutes before the product is separated. In a separation step, the admixture is then delivered to a steam distillation apparatus wherein 1-acetyl-1-chlorocyclopropane is azeotropically distilled with water and then condensed. The remaining salts and phase transfer catalyst are captured in the water of the steam distillation apparatus.

The reaction may be optionally run continuously in the presence of organic solvent. The product is then fractionally distilled away from the organic solvent after the initial azeotropic distillation.

EXAMPLES

Example 1

A 3-neck round-bottomed flask equipped with a reflux condenser and a magnetic stir bar was charged with aq. NaOH (38.5 g, 23%, 0.221 moles) and heated to 95° C. A mixture of 3,5-dichloro-2-pentanone (28.5 g, 98% pure, 0.18 moles) and methyltrioctylammonium chloride (in the commercial form of Aliquat 336, 2.0 g, 0.005 moles) heated to 90° C. in an addition funnel, was rapidly added to it in less than 5 seconds. The stirring was then started and the reaction mixture was stirred at 95° C. for 3 minutes. The flask was then plunged into ice-water bath. A weighed amount of internal standard (para-xylene) was added to it and stirred for 5 minutes while tightly closed. The layers were then allowed to separate and the organic layer was injected on GC. The yield was calculated using the predetermined response factor between 1-acetyl-1-chlorocyclopropane and para-xylene and was found to be 84.6% based on 3,5-dichloro-2-pentanone.

Example 2

A 3-neck round-bottomed flask equipped with a reflux condenser and a magnetic stir bar was charged with aq. NaOH (47.0 g, 23%, 0.27 moles) and heated to 95° C. A mixture of 3,5-dichloro-2-pentanone (28.5 g, 98% pure, 0.18 moles) and methyltrioctylammonium chloride (in the commercial form of Aliquat 336, 1.19 g, 0.0029 moles) heated to 90° C. in an addition funnel, was rapidly added to it in less than 5 seconds. The stirring was then started and the reaction mixture was stirred at 95° C. for 2 minutes. The reaction was then quenched by addition of aqueous hydrochloric acid (28.0 g, 9.8%, 0.075 moles). The product was then distilled out of the reaction mixture as an azeotrope with water at atmospheric pressure. A weighed amount of internal standard (para-xylene) was added to the distillate and stirred tightly closed. The layers were then allowed to separate and the organic layer was injected on GC. The yield was calculated using the predetermined response factor between 1-acetyl-1-chlorocyclopropane and para-xylene. The yield was found to be 83.0% based on 3,5-dichloro-2-pentanone.

Example 3

A 3-neck round-bottomed flask equipped with a reflux condenser and a magnetic stir bar was charged with aq. NaOH (32.4 g, 25%, 0.20 moles), 1,2-dichlorobenzene (20.1 g) and methyltrioctylammonium chloride (in the commercial form of Aliquat 336, 1.0 g, 0.0025 moles) and heated to 90° C. 3,5-dichloro-2-pentanone (28.5 g, 98% pure, 0.18 moles) was then added to it from an addition funnel over 3 hours. After the addition was over, the reaction mixture was cooked at 90° C. for 1 hour and then cooled to room temperature. The yield was determined using para-xylene as internal standard as in Example 1 and was found to be 84% based on 3,5-dichloro-2-pentanone.

Example 4

A 3-neck round-bottomed flask equipped with a reflux condenser and a magnetic stir bar was charged with aq. potassium carbonate (62.1 g, 47%, 0.21 moles) and heated to 95° C. A mixture of 3,5-dichloro-2-pentanone (28.5 g, 98% pure, 0.18 moles) and methyltributylammonium chloride (2.06 g, 75% aq. solution, 0.0066 moles) heated to 90° C. in an addition funnel, was rapidly added to it in less than 5 seconds. The stirring was then started and the reaction mixture was stirred at 95° C. for 15 minutes. The flask was then plunged into ice-water bath. A weighed amount of internal standard (para-xylene) was added to it and stirred for 5 minutes while tightly closed. The layers were then allowed to separate and the organic layer was injected on GC. The yield was calculated using the predetermined response factor between 1-acetyl-1-chlorocyclopropane and para-xylene and was found to be 82.9% based on 3,5-dichloro-2-pentanone. About 1.5% 3,5-dichloro-2-pentanone was found to be unreacted.

Example 5

A 3-neck round-bottomed flask equipped with a reflux condenser and a magnetic stir bar was charged with aq. potassium phosphate (58.4 g, 0.275 moles), water (58.4 g) and heated to 100° C. A mixture of 3,5-dichloro-2-pentanone (28.5 g, 98% pure, 0.18 moles) and methyltrioctylammonium chloride (in the commercial form of Aliquat 336, 2.08 g, 0.0051 moles) heated to 100° C. in an addition funnel, was rapidly added to it in less than 5 seconds. The stirring was then started and the reaction mixture was stirred at 100° C. for 20 minutes. The flask was then plunged into ice-water bath and diluted with 40 g water to dissolve all solids. The yield was determined as in Example 1 and was found to be 85.1% based on 3,5-dichloro-2-pentanone.

Example 6

A stream containing a mixture of 3,5-dichloro-2-pentanone (640 g/min, 95.5% pure, 3.94 moles/min) and methyltrioctylammonium chloride (in the commercial form of Aliquat 336, 46.3 g/min, 0.114 moles/min) preheated to 89° C. and a stream of aq. sodium hydroxide (23% solution, 999 g/min, 5.74 moles/min) preheated to 92° C. was fed simultaneously into an one inch diameter, 3 meter long tube packed with static mixers. The mean residence time for the reaction mixture inside the tube reactor was estimated to be about 1 min. The reaction mixture that came out the other end of the tube reactor was directly introduced into a steam distillation column. The product distilled over as an azeotrope with water while the salts, catalyst and impurities left the steam distillation column from the bottom. The yield of the product formed in the tube reactor was determined as follows: Initially the system was allowed to achieve a steady state under the above-mentioned flow rates. Then the reaction mixture that came out the other end of the tube reactor was diverted into a collection pot (instead of sending to the steam-distillation column) containing some cold water for a short time while at the same time noting down the amount of 3,5-dichloro-2-pentanone that entered the tube reactor in that time period. The amount of product in the collection pot was determined as in Example 1 and the yield of the product was found to be 82% based on 3,5-dichloro-2-pentanone.

Example 7

Three 3 liter jacketed cylindrical glass reactors were connected in series via dip tubes in such a way that the after a certain level is reached in the reactor, the pump between the reactors would pump the reactor contents via the dip tubes into the next reactor so that the level remained constant based on the position of the dip tubes. The second and the third reactors were fitted with a distillation head and condenser to distill out the product during the run. To begin the run, the first reactor jacket temperature was set to 106–107° C. and a stirred mixture of 3,5-dichloro-2-pentanone (98.8% pure) and 75% aqueous methyl-tributylammonium chloride (MTBCl) with a weight ratio of 15:1 was pumped in at a rate of 2.0 ml/min and at the same time a 47% aq. potassium carbonate solution was pumped into the same reactor at a rate of 3.6 ml/min. Under these conditions the mole ratio of 3,5-dichloro-2-pentanone:potassium carbonate:MTBCl entering the first reactor was 1.0:1.1:0.033. When the level in the first reactor reached 972 ml, the pump between reactor 1 and reactor 2 was started to pump the slurry into the second reactor. The level in the first reactor was maintained at around 972 ml by the position of the dip tube leading to the pump. In this way the three reactors were filled after a certain time. The jacket temperatures of the second and third reactors were kept about 15° C. higher than that of the first reactor. As the slurry came over in the second and third reactors the product was distilled overhead as an azeotrope with water. Most of the product was distilled over from reactor 2, any remaining product was recovered in the distillation from reactor 3. The yield of 1-acetyl-1-chlorocyclopropane was found to be 86% based on 3,5-dichloro-2-pentanone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of preparing 1-acetyl-1-chlorocyclopropane which comprises
    (a) providing 3,5-dichloro-2-pentanone;
    (b) providing a phase transfer catalyst selected from the group consisting of tetraalkylammonium halides and aryltrialkylammonium halides;
    (c) providing an aqueous solution of a base selected from the group consisting of bases whose conjugate acids have a $pK_a$ value in water of from about 8 to about 15;
    (d) admixing 3,5-dichloro-2-pentanone, the phase transfer catalyst, and the aqueous solution of the base at a temperature above room temperature in the absence of an organic solvent for a time sufficient to form 1-acetyl-1-chlorocyclopropane; and
    (e) separating the 1-acetyl-1-chlorocyclopropane.

2. The method of claim 1 wherein the aqueous solution contains at least one molar equivalent of base relative to the amount of 3,5-dichloro-2-pentanone.

3. The method of claim 1 wherein the base is sodium hydroxide or potassium hydroxide.

4. The method of claim 1 wherein the aqueous solution of base is an aqueous solution comprising from about 5% to about 50% by weight of sodium hydroxide.

5. The method of claim 1 wherein the aqueous solution of base is an aqueous solution comprising from about 10% to about 30% by weight of sodium hydroxide.

6. The method of claim 1 wherein the aqueous solution of base is an aqueous solution comprising from about 20% to about 25% by weight of sodium hydroxide.

7. The method of claim 1 wherein the phase transfer catalyst is a tetrabutylammonium halide and/or a methyltrialkylammonium halide.

8. The method of claim 1 wherein the phase transfer catalyst is methyltrioctylammonium chloride and/or methyltributylammonium chloride.

9. The method of claim 1 carried out as a continuous process.

10. The method of claim 9 wherein 3,5-dichloro-2-pentanone and the catalyst are introduced either separately or as a mixture into a flow of aqueous solution of base.

11. The method of claim 10 wherein the 3,5-dichloro-2-pentanone and/or the catalyst and/or the aqueous solution of base are preheated to a temperature of from about 70° C. to about 100° C. before introduction into the a reactor.

12. The method of claim 11 wherein in the separating step (e) the admixture from step (d) is introduced into a steam distillation apparatus.

13. The method of claim 12 wherein the time of admixing in step (d) until introduction into the steam distillation apparatus is from about 0.1 minutes to about 60 minutes.

14. The method of claim 12 wherein the time of admixing in step (d) until delivery into the steam distillation apparatus is from about 0.2 minutes to about 10 minutes.

15. The method of claim 12 wherein the time of admixing in step (d) until delivery into the steam distillation apparatus is from about 0.5 minutes to about 2 minutes.

16. The method of claim 1 wherein the ratio by weight of the 3,5-dichloro-2-pentanone to the phase transfer catalyst is from about 10:1 to about 100:1.

17. The method of claim 16 wherein the ratio is from 10:1 to 30:1.

18. The method of claim 16 wherein the ratio is from 12:1 to 16:1.

19. The method of claim 1 that is carried out as a batch process.

20. The method of claim 19 wherein the mixing time is from about 0.1 minutes to about 600 minutes.

21. The method of claim 20 wherein the base is sodium carbonate, potassium carbonate, sodium phosphate, potassium phosphate, sodium hydroxide or potassium hydroxide.

22. A method of preparing 1-acetyl-1-chlorocyclopropane which comprises
 (a) providing 3,5-dichloro-2-pentanone;
 (b) providing a phase transfer catalyst selected from the group consisting of tetraalkylammonium halides and aryltrialkylammonium halides;
 (c) providing an aqueous solution of a base selected from the group consisting of bases whose conjugate acids have a $pK_a$ value in water of from about 8 to about 15;
 (d) admixing 3,5-dichloro-2-pentanone, the phase transfer catalyst, and the aqueous solution of a base at a temperature above room temperature in the presence of an organic solvent that is substantially immiscible in water for a time sufficient to form 1-acetyl-1-chlorocyclopropane; and
 (e) separating the 1-acetyl-1-chlorocyclopropane.

23. The method of claim 22 wherein the solvent boils at a different temperature than 1-acetyl-1-chlorocyclopropane.

24. The method of claim 23 wherein the solvent is 1,2-dichlorobenzene.

25. The method of claim 24 wherein the base is sodium hydroxide, potassium hydroxide, sodium carbonate, potassium carbonate, sodium phosphate or potassium phosphate.

26. The method of claim 22 that is carried out continuously.

* * * * *